United States Patent [19]

Funaki et al.

[11] 4,203,995
[45] May 20, 1980

[54] 1-PHENYL-2-AZOLYL-4,4-DIMETHYL-1-PENTEN-3-OLS AND THE FUNGICIDAL USE THEREOF

[75] Inventors: Yuji Funaki, Toyonaka; Hirofumi Oshita, Takarazuka; Shizuya Tanaka, Minoo; Shigeo Yamamoto, Ikeda; Toshiro Kato, Ibaraki, all of Japan

[73] Assignee: Sumitomo Chemical Company, Limited, Osaka, Japan

[21] Appl. No.: 937,384

[22] Filed: Aug. 28, 1978

[30] Foreign Application Priority Data

Sep. 7, 1977 [JP] Japan .................... 52-108166

[51] Int. Cl.$^2$ ............ A01N 9/00; A01N 9/22; C07D 00/00
[52] U.S. Cl. .................... 424/273 R; 424/269; 542/458
[58] Field of Search ............ 424/269, 273 R; 542/458

[56] References Cited

U.S. PATENT DOCUMENTS

| | | | |
|---|---|---|---|
| 4,067,989 | 1/1978 | Shephard et al. | 542/458 |
| 4,086,351 | 4/1978 | Balasubramanyon et al. | 424/269 |

FOREIGN PATENT DOCUMENTS

| | | |
|---|---|---|
| 830733 | 12/1975 | Belgium . |
| 845433 | 2/1977 | Belgium . |
| 847001 | 4/1977 | Belgium . |
| 2610022 | 9/1976 | Fed. Rep. of Germany . |
| 2654890 | 8/1977 | Fed. Rep. of Germany . |
| 2734426 | 2/1978 | Fed. Rep. of Germany ........ 426/269 |

*Primary Examiner*—Douglas W. Robinson

*Attorney, Agent, or Firm*—Stevens, Davis, Miller & Mosher

[57] ABSTRACT

1-Phenyl-2-azolyl-4,4-dimethyl-1-penten-3-ols of the formula:

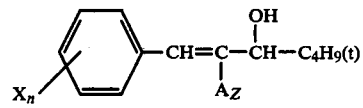

wherein X, which may be same or different, is an alkyl ($C_1$–$C_4$), cyano, alkoxy ($C_1$–$C_4$), phenoxy, phenyl group, halogen atom, n is zero or an integer of 1 to 2, $A_Z$ is an imidazole group of the formula

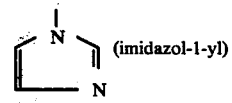 (imidazol-1-yl)

or a triazole group of the formula

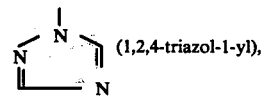 (1,2,4-triazol-1-yl), and salt thereof, which show high fungicidal activities without any material toxicity to mammals and plants and can be produced by reacting the corresponding 3-ketone compound with a reducing agent.

7 Claims, No Drawings

1-PHENYL-2-AZOLYL-4,4-DIMETHYL-1-PENTEN-3-OLS AND THE FUNGICIDAL USE THEREOF

The present invention relates to 1-phenyl-2-azolyl-4,4-dimethyl-1-penten-3-ols of the formula:

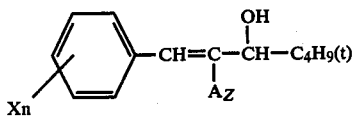

[I]

wherein X, which may be same or different, is an alkyl ($C_1$–$C_4$), cyano, alkoxy ($C_1$–$C_4$), phenoxy, phenyl group, or halogen, n is zero or an integer of 1 to 2, $A_Z$ is an imidazole group of the formula

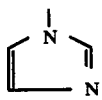

or a triazole group of the formula

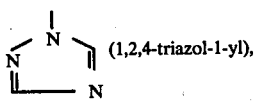 (1,2,4-triazol-1-yl), and salts thereof, and their preparation and use.

It is already known that some of α-azolyl pinacolone derivatives or α-azolyl acetophenone derivatives have an antimicrobial activity on certain microorganisms (Belgium patent Nos. 830733, 845433 and 847001, West Germany Patent Nos. 2610022 and 2654890). As the results of extensive study, it has now been found that the said compounds [I] having a benzylidene group and a hydroxy group exhibit an antimicrobial activity which is markedly superior and widely applicable as compared with their homologues, and in addition show no material phytotoxicity to plants and low mammalian toxicity.

Hitherto, a large number of organo-synthetic compounds and antibiotic substances having an antimicrobial activity have been found and developed as fungicides for agricultural purposes which have protected agricultural and horticultural crops from pathogens, thus having made a great contribution to the stable supply of agricultural products. Recently, it has become possible by the application of suitable fungicides to control soil-borne diseases and almost all the diseases except those owing to bacteria or virus.

But, the so-called resistance to pesticides of plant pathogens has come to be regarded as a serious practical problem for the past several years. In the fields wherein pesticides-resistant pathogens have appeared, it is often experienced that even the application of pesticides has little or no controlling effect on such pathogens. Also, the number of reports that resistant pathogens appeared against pesticides has increased.

The appearance of such resistant pathogens can certainly be inhibited by the alternate or mixed application of pesticides which act on pathogens in a different antimicrobial mechanism.

It is therefore necessary to develop agricultural fungicides which are different from the conventional ones in the antimicrobial mechanism and are superior in the disease controlling effect.

From the standpoints as described above, the inventors searched for novel compounds having an antimicrobial activity. As a result, it was found that the novel azole compounds of the formula [I] and their salts have an extremely strong controlling effect on diseases caused by fungi which are parasitic on agriculturally important crops, and at the same time that they have a strong antimicrobial activity on the so-called pesticides-resistant pathogens. Further, it was found that these compounds have a high degree of safety to mammals and fishes, and at the same time that they have the superior property as agricultural chemicals that they can be applied for practical purposes without doing any damage to agriculturally important crops.

As the diseases on which the compounds of the present invention can exert a strong controlling effect, there may be given rice blast (*Pyricularia oryzae*), sheath blight of rice (*Rhizoctonia solani*), blossom blight of apple (*Sclerotinia mali*), powdery mildew of apple (*Podosphaera leucotricha*), apple scab (*Venturia inaequalis*), fruit spot of apple (*Mycosphaerella pomi*), alternaria leaf spot of apple (*Alternaria mali*), black spot of pear (*Alternaria kikuchiana*), powdery mildew of pear (*Phyllactinia pyri*), rust of pear (*Gymnosporangium haraeanum*), scab of pear (*Venturia nashicola*), melanose of citrus (*Diaporthe citri*), citrus scab (*Elsinoe fawcetti*), common green mold of citrus fruit (*Penicillium digitatum*), blue mold of orange (*Penicillium italicum*), brown rot of peach (*Sclerotinia cinerea*), anthracnose of grape (*Elsinoe ampelina*), ripe rot of grape (*Glomerella cingulata*), gray mold of grape (*Botrytis cinerea*), powdery mildew of grape (*Uncinula necator*), rust of grape (*Phakopsora ampelopsidis*), crown rust of oats (*Puccinia coronata*), powdery mildew of barley (*Erysiphe graminis*), loose smut of barley (*Ustilago nuda*), covered smut of barley (*Ustilago hordei*), stem rust of barley (*Puccinia graminis*), leaf rust of wheat (*Puccinia recondita*), loose smut of wheat (*Ustilago tritici*), bunt of wheat (*Tilletia caries*), yellow rust of wheat (*Puccinia striiformis*), stem rust of wheat (*Puccinia graminis*), powdery mildew of wheat (*Erysiphe graminis*), powdery mildew of cucumber (*Sphaerotheca fuliginea*), gray mold of cucumber (*Botrytis cinerea*), sclerotinia rot of cucumber (*Sclerotinia sclerotiorum*), anthracnose of cucumber (*Colletotrichum lagenarium*), leaf mold of tomato (*Cladosporium fulvum*), powdery mildew of tomato (*Erysiphe cichoracearum*), early blight of tomato (*Alternaria solani*), gray mold of eggplant (*Botrytis cinerea*), powdery mildew of eggplant (*Erysiphe cichoracearum*), powdery mildew of pimento (*Leveillula taurica*), gray mold of strawberry (*Botrytis cinerea*), powdery mildew of strawberry (*Sphaerotheca humuli*), brown spot of tobacco (*Alternaria longipes*), powdery mildew of tobacco (*Erysiphe cichoracearum*) and the like.

The compounds of the present invention exerted the same strong antimicrobial activity on powdery mildew fungi of cucumber and gray mold fungi of grape already having a resistance to 1,2-bis(3-methoxycarbonyl-2-thioureido)benzene and methyl-N-benzimidazole-2-yl-N-(butylcarbamoyl)carbamate as on wild strains (susceptible strains). On further studying the antimicrobial activity of the present compounds, it became clear that some of them exert an antimicrobial activity on both *Trichopayton rubrum* and *Candida albicans* causing candidiasis. Thus, it was found that there is a possibility of the present compounds being usable as an antimycotic for medical purposes. Further, some compounds of the present invention have a plant growth regulating activity and a herbicidal activity.

The 1-phenyl-2-azolyl-4,4-dimethyl-1-penten-3-ols [I] can be prepared by the following process:

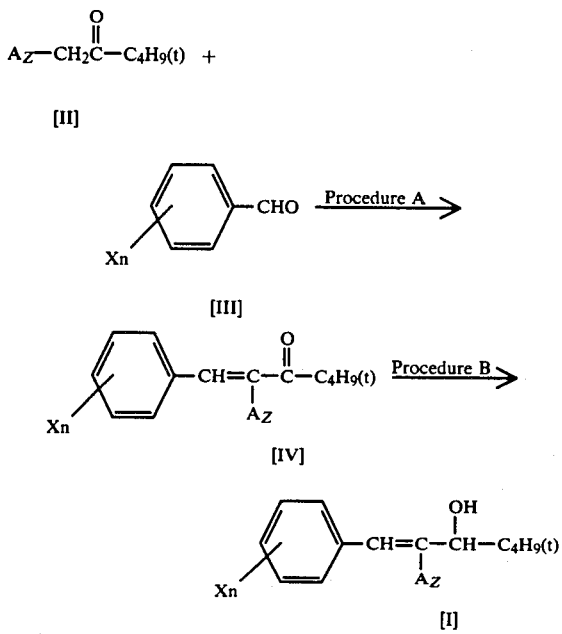

wherein $A_Z$, X and n are each as defined above.

Procedure A

The benzylideneketone compounds of the formula [IV] are produced by reacting 1 mole of α-azolyl pinacolone of the formula [II] with 1 to 2 moles of a benzaldehyde of the formula [III] in the presence of a basic catalyst. As the bases used for the reaction catalyst, there may be given alkali metal or alkaline earth metal hydroxides (e.g. sodium hydroxide, potassium hydroxide, calcium hydroxide), alkali metal alkoholate (e.g. sodium methylate, sodium ethylate, potassium methylate), carbonate (e.g. sodium carbonate, potassium carbonate) and secondary amines (e.g. diethylamine, dipropylamine, pyrrolidine, piperidine, morpholine). The benzylideneketone compounds of the formula [IV] can be obtained by carrying out the reaction at 0° to 120° C. in a solvent using 0.5 to 10.0 moles of the basic catalyst. As the solvent, there may be mentioned alcohols (e.g. methanol, ethanol, propanol, isopropanol, n-butanol), aromatic hydrocarbons (e.g. benzene, toluene, xylene), ethers (e.g. diethyl ether, tetrahydrofuran, dioxane), water and mixture thereof. When acetates such as sodium acetate and potassium acetate, or carbonates such as sodium carbonate and potassium carbonate are used as the bases, the reaction may be carried out at 15° to 120° C. in a reaction solvent such as glacial acetic acid or acetic anhydride using 0.5 to 10 moles of the base.

The starting α-azolylpinacolone [II] is obtainable, for instance, by the process as described in Belgium Patent Nos. 830733 and 845433.

Procedure B

The 1-phenyl-2-azolyl-4,4-dimethyl-1-penten-3-ols [I] are produced by reducing benzylideneketone compounds [IV] with a complex metalhydride (e.g. lithium aluminum hydride, sodium boron anhydride) or an aluminum alkoxide (e.g. aluminum isopropoxide) in a suitable solvent.

When the complex metal hydride is used, the solvent used includes ethers (e.g. diethyl ether, tetrahydrofuran, dioxane) and alcohols (e.g. methanol, ethanol, n-propanol, isopropanol).

When sodium boron hydride is used as the complex metal hydride, the reaction is achieved by mixing 1 mole of the compound of the formula [IV] and 0.25 to 1 mole of sodium boron hydride in a suitable solvent. The reaction temperature is preferably within the range of 0° C. to room temperature, and the solvent used includes ethers (e.g. diethyl ether, tetrahydrofuran, dioxane) and alcohols (e.g. methanol, ethanol, propanol, isopropanol).

When lithium aluminum hydride is used as the complex metal hydride, the reaction is achieved by adding dropwise a solution of lithium aluminum hydride in a suitable solvent to a solution of the compound [IV] in the same solvent. In this case, the amount of lithium aluminum hydride used is 0.25 time by mole based on the compound [IV]. The reaction temperature is preferably within the range of $-10°$ C. to $-60°$ C., and the solvent used includes ethers such as diethyl ether, tetrahydrofuran and the like. After the reaction is finished, water or a dilute aqueous acid solution is added to the reaction solution, followed by neutralization with an alkali if necessary and extraction with a water-insoluble organic solvent. The treatment thereafter is carried out in the usual manner.

When aluminum isopropoxide is used as the reducing agent, a preferred solvent is alcohols such as isopropanol or aromatic hydrocarbons such as benzene. The reaction is generally carried out at room temperature to 100° C. using 1 mole of the compound [IV] and 1 to 2 moles of aluminum isopropoxide. The aluminum compound obtained is decomposed with a dilute sulfuric acid or a sodium hydroxide solution, followed by extraction with an organic solvent. The treatment thereafter is carried out in the usual manner.

The salt of the compounds of the formula [I] is the salt of physiologically acceptable acids such as sulfuric acid, nitric acid, hydrohalogenic acids (e.g. hydrobromic acid, hydrochloric acid, hydroiodic acid), carboxylic acids (e.g. acetic acid, trichloroacetic acid, maleic acid, succinic acid), sulfonic acids (e.g. p-toluenesulfonic acid, methanesulfonic acid) and phosphoric acid. The salt of the compounds of the present invention is produced in the usual manner if necessary.

In the practical application of the present compounds thus obtained, they may be applied in a pure form with no other components, or in common preparation forms (e.g. dusts, wettable powders, oil sprays, emulsifiable concentrates, tablets, granules, fine granules, aerosols) by mixing them with a carrier for the ease of use as a fungicide.

The foregoing preparations generally contain 0.1 to 95.0% by weight, preferably 0.2 to 90.0% by weight of active ingredient (including other ingredients mixed). A suitable amount of active ingredient applied is generally 2 to 500 g per 10 are, and the concentration of active ingredient applied is preferably within the range of 0.001 to 1.0%. Since, however, the amount and concentration depend upon the preparation forms, application times, application techniques, application sites, diseases and crops, they may be properly increased or decreased irrespective of the aforesaid ranges.

Further, the compounds of the present invention may be applied in mixtures with other fungicides without lowering the controlling effect of each active ingredient of the mixture. As the fungicides there may be mentioned N-(3,5-dichlorophenyl)-1,2-dimethylcyclopropane-1,2-dicarboximide, S-n-butyl-S-p-tert-butylbenzyl-N-3-pyridyldithiocarbonimidate, O,O-dimethyl-O-2,6-dichloro-4-methylphenylphosphorothioate, methyl-N-benzimidazole-2-yl-N-(butylcarbamoyl)carbamate, N-trichloromethyl-thio-4-cyclohexene-1,2-dicarboximide, cis-N-(1,1,2,2-tetrachloroethylthio)-4-cyclohexene-1,2-dicarboximide, Polyoxin, Streptomycin, zinc ethylene-bis(dithiocarbamate), zinc dimethylthiocarbamate, manganese ethylene-bis(dithiocarbamate), bis(dimethylthiocarbamoyl) disulfide, tetrachloroisophthalonitrile, 8-hydroxyquinoline, dodecylguanidine acetate, 5,6-dihydro-2-methyl-1,4-oxathiine-3-carboxanilide, N'-dichlorofluoromethylthio-N,N-dimethyl-N'-phenylsulfamide, 1-(4-chlorophenoxy)-3,3-dimethyl-1-(1,2,4-triazole-1-yl)-2-butanone, 1,2-bis(3-methoxycarbonyl-2-thioureido)-benzene and the like. Further, the compounds of the present invention may be applied in mixtures with insecticides without lowering the controlling effect of each active ingredient of the mixture. As the insecticides, there may be mentioned O,O-dimethyl-O-(4-nitro-m-tolyl)phosphorothioate, O-p-cyanophenyl-O,O-dimethylphosphorothioate, O-p-cyanophenyl-O-ethylphenylphosphonothioate, O,O-dimethyl-S-(N-methylcarbamoylmethyl) phosphorodithioate, 2-methoxy-4H-1,3,2-benzodioxaphosphorine-2-sulfide, O,O-dimethyl-S-(1-ethoxycarbonyl-1-phenylmethyl)-phosphorodithioate, α-cyano-3-phenoxybenzyl-2-(4-chlorophenyl)-isovalerate, 3-phenoxybenzyl-2,2-dimethyl-3-(2,2-dichlorovinyl)cyclopropanecarboxylate, 3-phenoxybenzyl chrysanthemate and the like.

Consequently, two kinds or more of diseases and pests can be controlled at the same time and further a synergistic effect owing to mixing is also expected.

The present invention will be illustrated in more detail with reference to following examples of production.

EXAMPLE 1

1-p-Chlorophenyl-2-imidazol-1-yl-4,4-dimethyl-1-penten-3-ol (compound number 2)

Procedure A

A mixture of 1.0 g (0.006 mole) of α-imiazol-1-yl-pinacolone, 0.84 g (0.006 mole) of p-chlorobenzaldehyde, 10 ml of acetic anhydride and 0.4 g (0.003 mole) of potassium carbonate was kept at 50° C. for 3 hours. The reaction solution was poured into 100 ml of warm water (50° C.) to decompose acetic anhydride. Potassium carbonate was then added until the aqueous solution became alkaline, followed by extraction with 100 ml of ethyl acetate. The separated ethyl acetate layer was washed with water and dried over anhydrous sodium sulfate. The solvent was then removed under reduced pressure to obtain 1.1 g of a brown oily product. The product was purified by column chromatography on 50 g of silica gel (the product was eluted from silica gel with n-hexane/acetone (3:1) mixed solvent). Thus, 0.7 g of α-p-chlorobenzylidene-α-imidazol-1-yl-pinacolone was obtained in a yield of 40%. Melting point 99° C.

Elementary analysis:

| | C(%) | H(%) | N(%) | Cl(%) |
|---|---|---|---|---|
| Found | 66.51 | 5.96 | 9.77 | 12.66 |
| Calculated (as $C_{16}H_{17}N_2ClO$) | 66.54 | 5.95 | 9.70 | 12.27 |

Procedure B

Four grams (0.014 mole) of α-p-chlorobenzylidene-α-imidazol-1-yl-pinacolone was dissolved in 30 ml of methanol, and 150 mg (0.004 mole) of sodium boron hydride was added thereto, followed by stirring for 2 hours. After a 10% aqueous acetic acid solution was added to the reaction solution, followed by stirring for 1 hour, the reaction solution was neutralized with potassium carbonate and extracted with 100 ml of chloroform. The chloroform extract was washed with water, dried over anhydrous sodium sulfate and freed from the solvent under reduced pressure. The crystalline residue obtained was recrystallized from carbon tetrachloride to obtain 3.8 g of the entitled compound in a yield of 94%. Melting point 123°–124° C.

Elementary analysis:

| | C(%) | H(%) | N(%) | Cl(%) |
|---|---|---|---|---|
| Found | 66.13 | 6.50 | 9.57 | 12.07 |
| Calculated (as $C_{16}H_{19}N_2ClO$) | 66.09 | 6.59 | 9.63 | 12.19 |

EXAMPLE 2

1-(2',4'-Dichlorophenyl)-2-(1,2,4-triazol-1-yl)-4,4-dimethyl-1-penten-3-ol (compound number 14)

Procedure A

A mixture of 2.0 g (0.012 mole) of α-(1,2,4-triazol-1-yl)pinacolone, 2.1 g (0.012 mole) of 2,4-dichlorobenzaldehyde, 1.66 g (0.012 mole) of potassium carbonate and 30 cc of acetic anhydride was heated at 70° to 80° C. for 5 hours with stirring. The reaction solution was poured into warm water (50° C.), and potassium carbonate was added to make the aqueous solution alkaline, followed by extraction with 100 cc of ethyl acetate. The separated ethyl acetate layer was washed with water and dried over anhydrous sodium sulfate. The solvent was then removed under reduced pressure, and the oily residue obtained was purified by column chromatography on silica gel (n-hexane: acetone=10:1), followed by recrystallization from carbon tetrachloride. Thus, 1.0 g of α-2',4'-dichlorobenzylidene-α-(1,2,4-triazol-1-yl)-pinacolone was obtained in a yield of 26%. Melting point 119°–120° C.

Elementary analysis:

| | C(%) | H(%) | N(%) | Cl(%) |
|---|---|---|---|---|
| Found | 55.71 | 4.74 | 12.88 | 21.73 |
| Calculated (as $C_{15}H_{15}N_3Cl_2O$) | 55.57 | 4.66 | 12.96 | 21.87 |

Procedure B 3.2 g (0.01 mole) of α-2',4'-dichlorobenzylidene-α-(1,2,4-triazol-1-yl)pinacolone was dissolved in 30 ml of methanol and 150 mg (0.004 mole) of sodium boron hydride was added thereto. Thereafter, the procedure was carried out in the same manner as in Example 1 (procedure B) to obtain 3.0 g of the entitled compound in a yield 91%. Melting point 146°–147° C.

Elementary analysis:

| | C(%) | H(%) | N(%) | Cl(%) |
|---|---|---|---|---|
| Found | 55.20 | 5.22 | 12.90 | 21.75 |
| Calculated (as $C_{15}H_{17}N_3Cl_2O$) | 55.23 | 5.25 | 12.88 | 21.73 |

According to the above procedure, the 1-phenyl-2-azolyl-4,4-dimethyl-1-penten-3-ols [I] as shown in Table 1 are prepared.

Table 1

| Compound No. | Chemical structure | Physical constant |
|---|---|---|
| 1 | 2,3-diCl-phenyl-CH=C(imidazolyl)-CH(OH)-C$_4$H$_9$(t) | mp. 201°–203° C. |
| 2 | 4-Cl-phenyl-CH=C(imidazolyl)-CH(OH)-C$_4$H$_9$(t) | mp. 123°–124° C. |
| 3 | 4-Cl-phenyl-CH=C(imidazolyl)-CH(OH)-C$_4$H$_9$(t) hydrochloride | $n_D^{27.0}$ 1.5550 |
| 4 | 4-Cl-phenyl-CH=C(imidazolyl)-CH(OH)-C$_4$H$_9$(t) nitrate | $n_D^{27.0}$ 1.5540 |
| 5 | 4-NC-phenyl-CH=C(imidazolyl)-CH(OH)-C$_4$H$_9$(t) | mp. 193°–194° C. |
| 6 | 3-Br-2-CH$_3$O-phenyl-CH=C(imidazolyl)-CH(OH)-C$_4$H$_9$(t) | mp. 203°–204° C. |
| 7 | 2-F-phenyl-CH=C(imidazolyl)-CH(OH)-C$_4$H$_9$(t) | mp. 190°–191° C. |
| 8 | 2,4-diCl-phenyl-CH=C(imidazolyl)-CH(OH)-C$_4$H$_9$(t) | mp. 148°–149° C. |
| 9 | biphenyl-CH=C(imidazolyl)-CH(OH)-C$_4$H$_9$(t) | $n_D^{27.0}$ 1.5854 |
| 10 | 3-i-C$_3$H$_7$O-phenyl-CH=C(imidazolyl)-CH(OH)-C$_4$H$_9$(t) | mp. 172°–173° C. |
| 11 | 4-Cl-phenyl-CH=C(triazolyl)-CH(OH)-C$_4$H$_9$(t) | mp. 88°–90° C. |
| 12 | biphenyl-CH=C(triazolyl)-CH(OH)-C$_4$H$_9$(t) | mp. 172°–173° C. |
| 13 | 3-phenoxy-phenyl-CH=C(imidazolyl)-CH(OH)-C$_4$H$_9$(t) | $n_D^{29.0}$ 1.5780 |
| 14 | 2,4-diCl-phenyl-CH=C(triazolyl)-CH(OH)-C$_4$H$_9$(t) | mp. 146°–147° C. |
| 15 | 4-F-phenyl-CH=C(triazolyl)-CH(OH)-C$_4$H$_9$(t) | mp. 82°–85° C. |
| 16 | 4-Br-phenyl-CH=C(triazolyl)-CH(OH)-C$_4$H$_9$(t) | mp. 127°–128° C. |

Table 1-continued

| Compound No. | Chemical structure | Physical constant |
|---|---|---|
| 17 | F—⟨C6H4⟩—CH=C(−N(CH=CH−N=))—CH—C4H9(t), OH | $n_D^{21.0}$ 1.5137 |
| 18 | Br—⟨C6H4⟩—CH=C(−N(CH=CH−N=))—CH—C4H9(t), OH | mp. 117°–119° C. |
| 19 | C2H5O—⟨C6H4⟩—CH=C(−N(CH=CH−N=))—CH—C4H9(t), OH | Resinous substance |
| 20 | CH3—⟨C6H3(CH3)⟩—CH=C(−N(CH=CH−N=))—CH—C4H9(t), OH | mp. 97°–98° C. |
| 21 | ⟨C6H5⟩—CH=C(−N(CH=CH−N=))—CH—C4H9(t), OH | Resinous substance |

Procedures for preparing the fungicidal compositions of the present compounds are explained in detail below with reference to preparation examples, but the kinds and proportions of additives for the present compounds are variable within broad scopes without being limited to those shown in the examples. In the examples, all the parts are by weight.

Preparation Example 1 Dust

Two parts of the present compound 5, 88 parts of clay and 10 parts of talc are well pulverized. Thus, a dust containing 2% of active ingredient is obtained.

Preparation Example 2 Dust

Three parts of the present compound 4, 67 parts of clay and 30 parts of talc are well pulverized. Thus, a dust containing 3% of active ingredient is obtained.

Preparation Example 3 Wettable Powder

Thirty parts of the present compound 2, 30 parts of diatomaceous earth, 35 parts of white carbon, 3 parts of a wetting agent (sodium laurylsulfate) and 2 parts of a dispersing agent (calcium lignosulfonate) are well pulverized. Thus, a wettable powder containing 30% of active ingredient is obtained.

Preparation Example 4 Wettable Powder

Fifty parts of the present compound 7, 45 parts of diatomaceous earth, 2.5 parts of a wetting agent (calcium alkylbenzenesulfonate) and 2.5 parts of a dispersing agent (calcium lignosulfonate) are well pulverized. Thus, a wettable powder containing 50% of active ingredient is obtained.

Preparation Example 5 Emulsifiable Concentrate

Ten parts of the present compound 8, 80 parts of xylene and 10 parts of an emulsifying agent (polyoxyethylene alkylallyl ether) are mixed to obtain an emulsifiable concentrate containing 10% of active ingredient.

Preparation Example 6 Emulsifiable Concentrate

Thirty parts of the present compound 14, 60 parts of xylene and 10 parts of an emulsifying agent (polyoxyethylene alkylallyl ether) are mixed to obtain an emulsifiable concentrate containing 30% of active ingredient.

Preparation Example 7 Granule

Ten parts of the present compound 11, 85 parts of silica powder, 4.95 parts of calcium lignin sulfate and 0.05 part of sodium alkylbenzenesulfonate was well pulverized, kneaded with water, granulated, and then dried to obtain a granule containing 10% of active ingredient.

In order to substantiate excellent fungicidal effects of the present compounds, typical experimental results are described below with reference to experimental examples, but the experimental examples are part of typical experiments, and it is needless to say that the present compounds have extremely broad application scopes as fungicides.

Experimental Example 1

Protective Activity Test on Alternaria Sooty Spot of Chinese Cabbage (*Alternaria brassicicola*)

An aqueous diluted solution of the test compound in the form of an emulsifiable concentrate was sprayed on chinese cabbage (var. Nozaki No. 2), cultured in pots of 9 cm in diameter and almost grown up to the second leaf stage, at a rate of 7 ml per pot. After one day, a spore suspension of *Alternaria brassicicola* was sprayed on the surface of the leaves for inoculation. The plants were incubated in a dark and moist chamber for one day and then under illumination for 2 days. Then, the disease severity was determined in the following manner. Rates of infected area on the leaf were observed and classified in one of the disease indices (0, 1, 2, 4, 8) according to the undermentioned criteria. The disease severity was calculated according to the following equation.

| Disease index | Infectious state |
|---|---|
| 0 | No infected area on leaf surface |
| 1 | Infected area of less than 5% on leaf surface |
| 2 | Infected area of less than 30% on leaf surface |
| 4 | Infected area of less than 60% on leaf surface |
| 8 | Infected area of not less than 80% on leaf surface |

$$\text{Disease severity (\%)} = \frac{\Sigma(\text{Disease index} \times \text{number of leaves})}{5 \times (\text{Total number of leaves examined})} \times 100$$

The results of this test are shown in Table 2. As is apparent from the results, the compounds of the present invention showed a superior protective activity as compared with the analogous compounds which have already been reported.

Table 2

| Compound number | Concentration of active ingredient (ppm) | Disease severity (%) |
| --- | --- | --- |
| 7 | 500 | 27 |
| 8 | " | 25 |
| 9 | " | 19 |
| 18 | " | 23 |
| 19 | " | 3 |
| *1 | " | 100 |

*1 
[structure: CH₂–C(=O)–(2,4-dichlorophenyl), with N-(1,2,4-triazolyl) on CH₂]

| | | |
| --- | --- | --- |
| *1 | " | 100 |

[structure: CH₂–CH(OH)–(2,4-dichlorophenyl), with N-(1,2,4-triazolyl) on CH₂]

| | | |
| --- | --- | --- |
| *2 | " | 94 |

[structure: (4-chlorophenyl)–CH₂CH(N-triazolyl)–C(=O)–C₄H₉(t)]

| | | |
| --- | --- | --- |
| *3 | 500 | 59 |

[structure: Ph–CH₂CH(N-triazolyl)–CH(OH)–Ph]

| No treatment | — | 100 |

Note:
*1 The compounds disclosed in Belgium Pat. No. 830733
*2 The compound disclosed in Belgium Pat. No. 845433
*3 The compound disclosed in West Germany Pat. No. 2654890

Experimental Example 2

Protective Activity Test on Rice Blast (*Pyricularia oryzae*)

An aqueous diluted solution of the test compound in the form of an emulsifiable concentrate was sprayed on rice seedlings (var. Kinki No. 33), cultured in pots of 6.5 cm in diameter and almost grown up to the third leaf stage, at a rate of 10 ml per pot. After one day, a spore suspension of *Pyricularia oryzae* was sprayed on the surface of the leaves for inoculation. The plants were incubated in a dark and moist chamber for disease development. The disease severity was determined in the manner described in Experimental example 1.

The results of this test are shown in Table 3. As is apparent from the results, the compounds of the present invention showed a superior protective activity as compared with analogous compounds which have already been reported.

Table 3

| Compound number | Concentration of active ingredient (ppm) | Disease severity (%) |
| --- | --- | --- |
| 2 | 500 | 19 |
| 4 | " | 17 |
| 8 | " | 23 |
| 9 | " | 25 |
| 12 | " | 20 |
| 13 | " | 15 |
| 17 | " | 3 |
| 18 | " | 17 |
| 19 | " | 12 |
| 20 | " | 19 |
| *1 | " | 100 |

[structure: CH₂C(=O)C₄H₉(t), with N-(1,2,4-triazolyl) on CH₂]

| | | |
| --- | --- | --- |
| *1 | " | 100 |

[structure: CH₂–C(=O)–(2,4-dichlorophenyl), with N-(1,2,4-triazolyl) on CH₂]

| | | |
| --- | --- | --- |
| *1 | " | 100 |

[structure: CH₂–CH(OH)–(2,4-dichlorophenyl), with N-(1,2,4-triazolyl) on CH₂]

| | | |
| --- | --- | --- |
| *2 | " | 67 |

[structure: (4-chlorophenyl)–CH₂CH(N-triazolyl)–C(=O)–C₄H₉(t)]

| | | |
| --- | --- | --- |
| *3 | " | 92 |

[structure: Ph–CH₂CH(N-triazolyl)–C(=O)–Ph]

| | | |
| --- | --- | --- |
| *4 | " | 100 |

[structure: Ph–CH₂CH(N-triazolyl)–CH(OH)–Ph]

| No treatment | — | 100 |

Note:
*1 The compounds disclosed in Belgium Pat. No. 830733
*2 The compound disclosed in Belgium Pat. No. 845433
*3 The compound disclosed in West Germany Pat. No. 2610022
*4 The compound disclosed in West Germany Pat. No. 2654890

The present invention will be illustrated in more detail with reference to the following experimental examples and preparation examples. But, the present invention is not of course limited to these examples.

Experimental Example 3

Protective Activity Test on Powdery Mildew of Cucumber (*Sphaerotheca fuliginea*)

Cucumber (var. Sagami-hanjiro) was cultivated in a flower pot of 9 cm in diameter. When it opened the cotyledon, each of the emulsifiable concentrates of the present compounds was diluted with water to a predetermined concentration, and sprayed on the cucumber at a rate of 15 ml per pot. After the test liquor was dried, the cucumber was inoculated by spraying the spore suspension of *Sphaerotheca fuliginea*, and cultivated at a room temperature of 27° C. for 10 days under fluorescent lighting. Thereafter, the infectious state was observed.

The disease severity was calculated by the following method: The leaves examined were measured for a percentage of infected area and classified into the corresponding disease indices, 0, 1, 2, 3, 4, 5; and the disease severity was calculated according to the following equation.

| Disease index | Infectious state |
|---|---|
| 0 | No infected area on leaf surface |
| 1 | Infected area of less than 10% on leaf surface |
| 2 | Infected area of less than 30% on leaf surface |
| 3 | Infected area of less than 60% on leaf surface |
| 4 | Infected area of less than 80% on leaf surface |
| 5 | Infected area of not less than 80% on leaf surface |

$$\text{Disease severity (\%)} = \frac{\Sigma(\text{Disease index} \times \text{number of leaves})}{5 \times (\text{Total number of leaves examined})} \times 100$$

The results of this test are shown in Table 4. As is apparent from the results, the compounds of the present invention showed a superior protective activity as compared with the control compound.

Table 4

| Compound Number | Concentration of active ingredient (ppm) | Disease severity (%) |
|---|---|---|
| 1 | 500 | 0.0 |
| 2 | " | " |
| 3 | " | " |
| 4 | " | " |
| 5 | " | " |
| 6 | " | " |
| 7 | " | " |
| 8 | " | " |
| 9 | " | " |
| 10 | " | " |
| 11 | " | " |
| 12 | " | " |
| 13 | " | " |
| 14 | " | " |
| 15 | " | " |
| 16 | " | " |
| 17 | " | " |
| 18 | " | " |
| 19 | " | " |
| 20 | " | " |
| 21 | " | " |
| *1 (structure: benzimidazole-NHCOOCH₃, N-CONHC₄H₉) | " | 2.5 |
| No treatment | — | 1000 |

Note:
*1 Fungicide, methyl-1-(butylcarbamoyl)-benzimidazole-2-yl-carbamate

Experimental Example 4

Protective Activity Test on Powdery Mildew of Barley (*Erysiphe graminis*)

Barley (var. Goseshikoku) was cultivated in a flower pot of 9 cm in diameter. When it was grown up to a first leaf stage, each of the emulsifiable concentrates of the present compounds was diluted with water to a pre-determined concentration, and sprayed on the barley at a rate of 15 ml per pot. After the test liquor was air-dried, the barley was inoculated with *Erysiphe graminis*, and cultivated under fluorescent lighting in a constant temperature room of 23° C. for 10 days. Thereafter, the infectious state was observed. The disease severity was calculated in the same manner as in Experimental example 3.

The results of this test are shown in Table 5. As is apparent from the results, the compounds of the present invention showed the same superior protective activity as that of the control compound.

Table 5

| Compound number | Concentration of active ingredient (ppm) | Disease severity (%) |
|---|---|---|
| 1 | 200 | 0.0 |
| 2 | " | " |
| 3 | " | " |
| 4 | " | " |
| 5 | " | " |
| 6 | " | " |
| 7 | " | " |
| 8 | " | " |
| 9 | " | " |
| 10 | " | " |
| 11 | " | " |
| 12 | " | " |
| 13 | " | " |
| 14 | " | " |
| 15 | " | " |
| 16 | " | " |
| 17 | " | " |
| 18 | " | " |
| 19 | " | " |
| 20 | " | " |
| 21 | " | " |
| *1 (2,6-dimethylmorpholine with N—C₁₃H₂₇) | " | " |
| No treatment | — | 100.0 |

Note:
*1 Fungicide, 2,6-dimethyl-4-tridecylmorpholine

Experimental Example 5

Protective Activity Test on Crown Rust of Oats (*Puccinia coronata*)

When oats (var. Zenshin) cultivated in a flower pot of 9 cm in diameter were grown up to a first leaf stage, the oats were inoculated with *Puccinia coronata* and placed in a humid chamber for 16 hours. Thereafter, each of the emulsifiable concentrates of the present compounds was diluted with water to a pre-determined concentration, and sprayed on the oats at a rate of 15 ml per pot. The oats were then cultivated under fluorescent lighting in a constant temperature room of 23° C. for 10 days. Thereafter, the infectious state was observed. The disease severity was calculated in the same manner as in Experimental example 3.

The results of this test are shown in Table 6. As is apparent from the results, the compounds of the present invention showed a superior protective activity as compared with the control compound.

Table 6

| Compound number | Concentration of active ingredient (ppm) | Disease severity (%) |
| --- | --- | --- |
| 2 | 500 | 0.0 |
| 3 | " | " |
| 4 | " | " |
| 5 | " | " |
| 6 | " | " |
| 7 | " | " |
| 8 | " | " |
| 10 | " | " |
| 11 | " | " |
| 14 | " | " |
| 15 | " | " |
| 16 | " | " |
| 17 | " | " |
| OHCNH–CH(Cl$_3$C)–N(piperazine)N–CH(CCl$_3$)–NHCHO  *1 | " | 7.0 |
| No treatment | — | 100.0 |

Note:
*1 Fungicide, N,N'-bis(1-formamido-2,2,2-trichloroethyl)piperazine

Experimental Example 6

Systemic Activity Test on Crown Rust of Oats (*Puccinia coranata*)

Oats (var. Zenshin) were planted in a flower pot of 6.5 cm in diameter, grown up to a first leaf stage, and used as test plants. An aqueous diluted solution of the test compound in the form of an emulsifiable concentrate was applied to the soil in the pot at a rate of 20 ml per pot. The oat seedlings, which were planted in the soil treated with the test compound, were cultivated for 3 days in a greenhouse and then inoculated with *Puccinia coronata* as described in Experimental example 5. After cultivating the plants at 23° C. for 10 days, the disease severity was assessed in the manner mentioned in Experimental example 3.

The results of this test are shown in Table 7. As is apparent from the results, the compounds of the present invention showed a superior systemic activity as compared with analogous compounds which have already been reported.

Table 7

| Compound number | Concentration of active ingredient (ppm) | Disease severity (%) |
| --- | --- | --- |
| 2 | 200 | 0 |
|  | 100 | " |
| 11 | 200 | " |
|  | 100 | " |
| 14 | 200 | " |
|  | 100 | " |
| 15 | 200 | " |
|  | 100 | " |
| 16 | 200 | " |
|  | 100 | " |
| imidazole-CH$_2$C(O)–C$_4$H$_9$(t)  *1 | 200 | 100 |
| Cl–C$_6$H$_4$–CH$_2$CH(imidazole)–C(O)–C$_4$H$_9$(t)  *2 | " | 31 |
| Cl–C$_6$H$_4$–CH$_2$CH(imidazole)–C(O)–C$_4$H$_9$(t)  *2 | " | 44 |

Table 7-continued

| Compound number | Concentration of active ingredient (ppm) | Disease severity (%) |
|---|---|---|
| 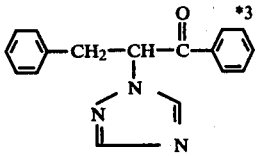 *3 | " | 100 |
| 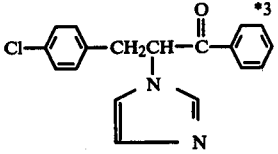 *3 | " | 64 |
| 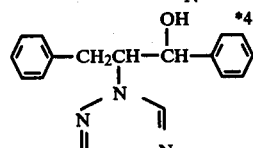 *4 | " | 100 |
| 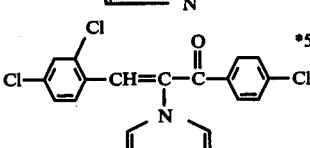 *5 | " | 80 |
| No treatment | — | 100 |

Note:
*1 The compound disclosed in Belgium Pat. No. 830733
*2 The compounds disclosed in Belgium Pat. No. 845433
*3 The compounds disclosed in West Germany Pat. No. 2610022
*4 The compound disclosed in West Germany Pat. No. 2654890
*5 The compound disclosed in Belgium Pat. No. 847001

What is claimed is:

1. A compound of formula:

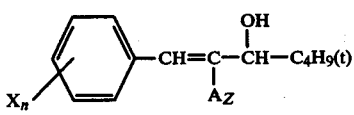

wherein X, which may be same or different, is alkyl ($C_1$-$C_4$), cyano, alkoxy ($C_1$-$C_4$), phenoxy, phenyl or halogen, n is zero or an integer of 1 to 2, $A_Z$ is an imidazole group of the formula

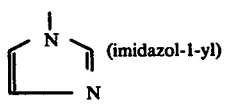    (imidazol-1-yl)

or triazole of the formula

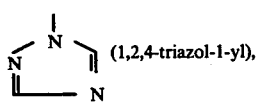    (1,2,4-triazol-1-yl), or salts thereof.

2. The compound according to claim 1, wherein X is halogen substituted at 4-position, $A_Z$ is an imidazole group of the formula

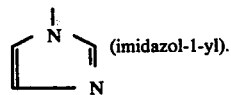    (imidazol-1-yl).

3. The compound according to claim 1, wherein X is a halogen atom substituted at the 4-position, $A_Z$ is a triazole group of the formula

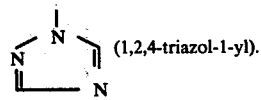    (1,2,4-triazol-1-yl).

4. The compound according to claim 1, wherein X is halogen substituted, at the 2,4-positions, $A_Z$ is an imidazole group of the formula

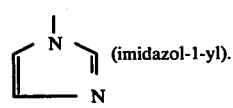    (imidazol-1-yl).

5. The compound according to claim 1, wherein X is halogen substituted at the 2,4-positions, $A_Z$ is a triazole group of the formula

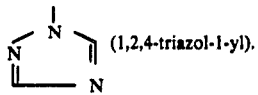 (1,2,4-triazol-1-yl).
6. A fungicidal composition which comprises as an active ingredient a fungicidally effective amount of the compound according to claim 1 and an inert carrier.
7. A method for killing fungi which comprises applying a fungicidally effective amount of the compound according to claim 1 to the fungi.
* * * * *